United States Patent [19]

Fanshawe et al.

[11] 3,935,211

[45] Jan. 27, 1976

[54] CYCLOPROPYL 1,2,4-OXADIAZOLYLDIAZINES

[75] Inventors: William Joseph Fanshawe, Pearl River, N.Y.; Sidney Robert Safir, River Edge, N.J.

[73] Assignee: American Cyanamid Company, Stamford, Conn.

[22] Filed: Aug. 20, 1974

[21] Appl. No.: 498,901

Related U.S. Application Data

[62] Division of Ser. No. 347,307, April 2, 1973, Pat. No. 3,857,843, which is a division of Ser. No. 288,219, Sept. 11, 1972, Pat. No. 3,770,739.

[52] U.S. Cl................................................ 260/250 A
[51] Int. Cl.² ...................................... C07D 237/14
[58] Field of Search ................. 260/250 A, 250 AH

[56] References Cited

UNITED STATES PATENTS 3,705,157  12/1972  Wiegand et al.................. 260/250 A

*Primary Examiner*—Donald G. Daus
*Assistant Examiner*—Anne Marie T. Tighe
*Attorney, Agent, or Firm*—Norton S. Johnson

[57] ABSTRACT

Preparation of 1,2,4-oxadiazolyldiazines by the reaction of cyclopropylcarboxylic acid anhydride and a diazinecarboxamidoxime at an elevated temperature. Other methods are also described. The compounds are useful for their central nervous system depressant activity.

2 Claims, No Drawings

CYCLOPROPYL 1,2,4-OXADIAZOLYLDIAZINES

DESCRIPTION OF THE INVENTION

This invention relates to new 1,2,4-oxadiazolyldiazines which may be illustrated by the following formula:

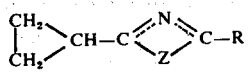

wherein R is a pyridazinyl radical; Z is a trivalent radical selected from the group consisting of

and

and the dotted line represents one double bond, the position of which is dependent upon the definition of Z. When Z is

the double bond is between N and carbon containing the R substituent and when Z has the other meaning, the double bond is in the other position.

Pharmaceutically acceptable acid addition salts are considered to be within the purview of the present invention and can be prepared by direct neutralization of the free base with the appropriate acid. These salts are those in which the anion does not contribute significant toxicity to the salt in the dosages thereof employed in accordance with the present invention. Examples of suitable salts are the acetate, propionate, butyrate, pamoate, mucate, citrate, malate, tosylate, phosphate, nitrate, sulfate, hydrobromide, hydroiodide, hydrochloride, etc.

The present compounds are somewhat soluble in hydrocarbon solvents. The salts of the compounds are slightly soluble in water.

The compounds of the present invention can be prepared by reaction of cyclopropylcarboxylic acid anhydride and a diazinecarboxamidoxime at elevated temperature in the presence or absence of a solvent. The compounds are also prepared by the reaction of a diazinecarboxylic acid chloride or of an ester of a diazinecarboxylic acid with cyclopropylcarboxamidoxime in the presence of solvent at an elevated temperature.

These reactions are illustrated schematically below:

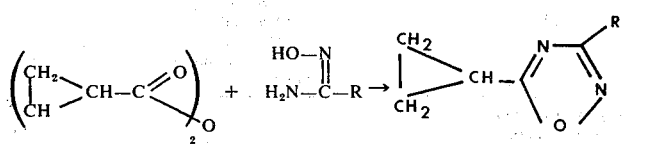

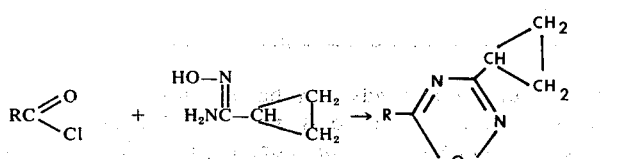

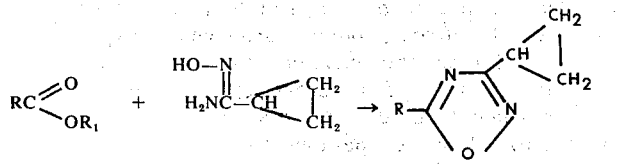

wherein R is as defined above and $R_1$ is methyl or ethyl.

Among the compounds considered to be within the scope of the present invention are:
3-{5-cyclopropyl-1,2,4-oxadiazol-3-yl}pyridazine
3-{3-cyclopropyl-1,2,4-oxadiazol-5-yl}pyridazine
4-{5-cyclopropyl-1,2,4-oxadiazol-3-yl}pyridazine
4-{3-cyclopropyl-1,2,4-oxadiazol-5-yl}pyridazine The compounds of this invention show central nervous system depressant activity by their ability to protect warmblooded animals, e.g., mice, from convulsions and lethality resulting from the administration of strychnine sulfate [H. M. Hanson and C. A. Stone, "Animal and Clinical Pharmacological Techniques in Drug Evaluation," Vol. I, J. H. Nodine and P. E. Siegler, Eds. Yearbook Medical Publishers, Inc., Chicago, Ill., 1964, p. 317]. Graded dose levels of the compounds are administered intraperitoneally in a 2% aqueous starch medium to groups of ten mice at each dose. Strychnine sulfate, dissolved in aqueous saline is administered subcutaneously 30 minutes after drug treatment at a dose estimated to cause death in 95% of the mice; namely, 1.25 mg. per kilogram of body weight. The medium effective dose is calculated by the method of J. T. Litchfield and F. Wilcoxon [J. Pharmacol. Exp. Ther., 96, 99 (1949)]. These data on representative compounds of this invention are summarized in Table I. It has been reported [M. I. Gluckman, Pharmacology of oxazepam (Serax) an antianxiety agent, Curr. Therap. Res., 1, 721 (1965)] that there is a high degree of correlation between anticonvulsant effects in mice and antianxiety effects in higher warm-blooded animals.

TABLE I

Protection Against Death Caused by Strychnine Sulfate in Mice

| Compound | Median Effective Dose (mg./kg. intraperitoneally) for protection versus death caused by strychnine |
| --- | --- |
| 2-(5-cyclopropyl-1,2,4-oxadiazol-3-yl)pyrazine | 3.5 |
| 4-(5-cyclopropyl-1,2,4-oxadiazol-3-yl)-pyridazine | 6.0 |
| 4-(5-cyclopropyl-1,2,4-oxadiazol-3-yl)pyrimidine | 27 |
| 2-(3-cyclopropyl-1,2,4-oxadiazol-5-yl)pyrazine | 39 |

The present compounds may be dispensed in the form of capsules, tablets, pills, powders, dispersible granules and cachets. One or more of the following may act as solid pharmaceutical carrier flavoring agents, binders, tablet disintegrating agents, encapsulating material and the like. Other solid carriers can be, for example, magnesium carbonate or stearate, talc, sugar, lactose, pectin, dextrin, starch, gelatin, tragacanth, methyl cellulose, sodium carboxymethyl cellulose, etc. Preferably, the active component may represent a major portion of the dosage unit. The present compounds may be used in dosages which range from about 0.1 to 100 mg./kg./per day in warmblooded animals. The warm-blooded animals may include mice, rats, guinea pigs, dogs, rabbits, sheep, etc. A dosage unit may range from 10 to 150 mg. given one or more times per day. It is usually preferable to give more than one dosage unit per day at predetermined intervals.

DETAILED DESCRIPTION

The examples which follow describe the preparation of representative novel compounds of the present invention.

EXAMPLE 1

Preparation of 2-(5-cyclopropyl-1,2,4-oxadiazol-3-yl)pyrazine

A mixture of 6.9 g. of pyrazinecarboxamidoxime and 7.7 g. of cyclopropanecarboxylic acid anhydride in 100 ml. of xylene is heated under reflux for 3 hours. The xylene is evaporated under reduced pressure and the residue is suspended in aqueous sodium carbonate. The mixture is filtered to collect tan crystals which are recrystallized from isopropyl alcohol to give straw-colored crystals, melting point 95°–98°C. The compound forms a slightly water soluble hydrochloride salt.

EXAMPLE 2

Preparation of 2-(5-methyl-1,2,4-oxadiazol-3-yl)pyrazine

A stirred mixture of 2.8 g. of pyrazinecarboxamidoxime and 2.0 g. of acetic anhydride in 50 ml. of xylene is heated under reflux for 3 hours. The xylene is evaporated under reduced pressure and the residue is recrystallized twice from isopropyl alcohol to give white crystals, melting point 100°–104°C.

EXAMPLE 3

Preparation of 2-(5-ethyl-1,2,4-oxadiazol-3-yl)pyrazine

A stirred mixture of 2.8 g. of pyrazinecarboxamidoxime and 2.6 g. of propionic anhydride in 50 ml. of xylene is heated under reflux for 3 hours and concentrated to a viscous liquid. The liquid is suspended in aqueous sodium carbonate and the mixture is extracted with chloroform. The chloroform solution is dried over anhydrous magnesium sulfate and concentrated to a solid. Recrystallization from hexane gives white crystals, melting point 52°–57°C.

EXAMPLE 4

Preparation of 4-(5-Cyclopropyl-1,2,4-oxadiazol-3-yl)pyridazine

A mixture of 2.8 g. of 4-pyridazinecarboxamidoxime and 3.1 g. of cyclopropanecarboxylic acid anhydride in 50 ml. of xylene is heated under reflux for 3 hours. The mixture is filtered and the collected solid is suspended in aqueous sodium carbonate. The mixture is filtered and the collected solid partially dissolved in hot ethanol and filtered. The filtrate is concentrated to tan crystals which are recrystallized from ethanol to give cream-colored crystals, melting point 115°–117°C. The compound forms a slightly water soluble sulfate salt, when treated with sulfuric acid.

EXAMPLE 5

Preparation of 4-(5-ethyl-1,2,4-oxadiazol-3-yl)pyridazine

A mixture of 0.92 g. of 4-pyridazinecarboxamidoxime, 1.05 g. of propionic anhydride and 20 ml. of xylene is heated under reflux for 2 hours. The mixture is washed with 1 N sodium hydroxide, the xylene solution dried over magnesium sulfate and concentrated to give a tan solid. This solid is recrystallized from cyclohexane to give colorless needles, melting point 73°–74°C.

EXAMPLE 6

Preparation of 4-(5-cyclopropyl-1,2,4-oxadiazol-3-yl)pyrimidine

A mixture of 1.4 g. of 4-pyrimidinecarboxamidoxime and 1.5 g. of cyclopropanecarboxylic acid anhydride in 20 ml. of xylene is heated under reflux for 3 hours. The mixture is concentrated to give a viscous, orange liquid which is suspended in aqueous sodium carbonate and then filtered to collect an orange solid. This solid is recrystallized from cyclohexane to give pale yellow crystals, melting point 89°–94°C. The compound forms

EXAMPLE 7

Preparation of
2-(3-Cyclopropyl-1,2,4-oxadiazol-5-yl)pyrazine

To a mixture of 28.7 g. of pyrazinoyl chloride in 100 ml. of xylene is added slowly a solution of 20 g. of cyclopropanecarboxamidoxime in 100 ml. of xylene. This mixture is heated under reflux for 3 hours, concentrated under reduced pressure and the residue mixed with aqueous sodium hydroxide. The mixture is filtered and the filtrate is extracted with chloroform. The chloroform solution is dried over magnesium sulfate and concentrated under reduced pressure to give crude crystals, which are recrystallized from cyclohexane to give light yellow crystals, melting point 61°–64°C.

EXAMPLE 8

Preparation of
2-(3-Cyclopropyl-1,2,4-oxadiazol-5-yl)pyrazine

To a mixture of 2.8 g. of cyclopropanecarboxamidoxime hydrochloride and 2.8 g. of methyl pyrazinoate in 50 ml. of toluene is added 2.2 g. of sodium methoxide. The mixture is heated under reflux for 30 minutes and then poured into 100 ml. of water. The toluene phase is separated and the aqueous phase is extracted with chloroform. The combined organic solutions are dried over magnesium sulfate and concentrated under reduced pressure to give a solid. This solid is recrystallized from cyclohexane to give cream-colored crystals, melting point 66°–68°C. The compound forms a slightly water soluble phosphate salt, when treated with phosphoric acid.

We claim:

1. A cyclopropyl-1,2,4-oxadiazolyldiazine of the formula:

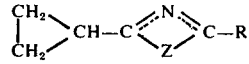

wherein Z is a trivalent radical selected from the group consisting of

and

the dotted line represents one double bond, the position being dependent upon the definition of Z; R is pyridazinyl and a pharmaceutically acceptable salt thereof.

2. The cyclopropyl-1,2,4-oxadiazolylpyridazine according to claim 1: 4-(5-cyclopropyl-1,2,4-oxadiazol-3-yl)-pyridazine.

* * * * *